United States Patent [19]
Heidsieck et al.

[11] Patent Number: 5,539,797
[45] Date of Patent: Jul. 23, 1996

[54] METHOD AND APPARATUS FOR DIGITAL STEREOTAXIC MAMMOGRAPHY

[75] Inventors: Robert Heidsieck, Le Chesnay; Jean-Pierre Saladin, Bagneux; Serge Muller, Guyancourt, all of France

[73] Assignee: GE Medical Systems SA, Buc, France

[21] Appl. No.: 218,931

[22] Filed: Mar. 29, 1994

[30] Foreign Application Priority Data

Mar. 29, 1993 [FR] France ................... 93 03614

[51] Int. Cl.$^6$ ...................................... A61B 6/04
[52] U.S. Cl. ............................. 378/37; 378/196
[58] Field of Search ........................ 378/37, 41, 42, 378/17, 98, 189, 190, 193, 195, 196, 197, 98.8, 62

[56] References Cited

U.S. PATENT DOCUMENTS

| | | | |
|---|---|---|---|
| 3,963,932 | 6/1976 | Ohno et al. | 250/445 |
| 4,158,777 | 6/1979 | Hogan | 250/445 |
| 4,727,565 | 2/1988 | Ericson | 378/37 |
| 5,018,176 | 5/1991 | Romeas et al. | 378/37 |
| 5,078,142 | 1/1992 | Sczek et al. | 128/653.1 |
| 5,142,557 | 8/1992 | Toker et al. | 378/37 |
| 5,166,969 | 11/1992 | Heidsieck | 378/207 |
| 5,218,625 | 6/1993 | Heidsieck | 378/97 |
| 5,289,520 | 2/1994 | Pellegrino et al. | 378/208 |

FOREIGN PATENT DOCUMENTS

| | | |
|---|---|---|
| 0181520 | 5/1986 | European Pat. Off. |
| 0395458 | 10/1990 | European Pat. Off. |
| WO-A-9005485 | 5/1990 | WIPO |

Primary Examiner—David P. Porta
Assistant Examiner—Don Wong
Attorney, Agent, or Firm—Nilles & Nilles

[57] ABSTRACT

A mammograph is disclosed which includes: a positioning device defining a rotation axis, the positioning device including: an arm $\beta_2$; breast support plate connected to the arm $\beta_2$; a movement device connected to the arm $\beta_2$; and a digital detector connected to the movement device, the digital detector having a detection surface defining a plane $\pi$; an arm $\beta_1$ pivotally connected to the positioning device for pivotally rotating said arm $\beta_1$ around said rotation axis, the arm $\beta_1$ having an end; and an X-ray tube movably attached to the end of the arm $\beta_1$, the X-ray tube defining a beam axis $\delta$ and being pivotable about the rotation axis so as to move in a first direction that is orthogonal with the rotation axis and direct an X-ray beam, emitted by the X-ray tube, along the beam axis $\delta$. Pivoting the X-ray tube within an angle $\pm\alpha$ causes the movement device to move the digital detector laterally within the plane $\pi$ along a second direction that is perpendicular to the rotation axis and opposite the first direction so as to accommodate a position of the X-ray tube within the angle $\pm\alpha$ and define a volume of a breast stereotaxically accessible by the X-ray beam as a polyhedron having a first surface and a second surface, the first surface and the second surface meeting and being defined by an intersection of the beam axis $\delta$ at an angle $\pm\alpha$ with the beam axis $\delta$ at an angle $-\alpha$, the X-ray beam being entirely incident the digital detector as the movement device moves the digital detector to accommodate pivotal movement of the X-ray tube.

18 Claims, 3 Drawing Sheets

METHOD AND APPARATUS FOR DIGITAL STEREOTAXIC MAMMOGRAPHY

BACKGROUND OF THE INVENTION

1. Field of the Invention

The present invention relates to a mammograph equipped with a stereotaxic imaging device with digital detector and a method of using such a mammograph. The field of use of the invention is essentially medical, since mammography makes it possible to detect tumors of the breast and to carry out certain medical treatments.

2. Discussion of the Related Art

A mammograph comprises an X-ray tube, situated at the end of a first arm which can be moved about an axis and emitting X-radiation toward a receiver situated at the end of another arm. A breast support plate and a breast compression plate, holding the breast in place during mammography, are arranged between the tube and the receiver. The image receiver may be a photographic film or a digital receiver, such as a CCD camera. In order to take stereotaxic images, it is necessary for the X-ray tube to be movable in rotation, about the breast support and compression plates, in order to be inclined successively along two opposite orientations on either side of its initial position which is perpendicular to the plane of the image receiver, so that two images are taken by the receiver. By virtue of a stereotaxic location device carrying out the computerized processing of the two images obtained after developing of the photographic frames, the three-dimensional position of a defined region of the breast, where, for example, there is a lesion, is calculated. A mammograph equipped with such a stereotaxic imaging device is described in the European Patent published under number 0,390,653 B1 in the name of the Applicant Company.

In order to reduce the duration of the radiological examination which is relatively painful for the patient, in particular during medical treatments during which it is necessary to develop the photographic film, calculate the position of the region to be treated, and guide the biopsy needle, for example, before ending the compression of the breast, the film is replaced by a digital detector. Digital detectors are currently made from CCD sensors which make it possible to obtain a digitized image of the object examined in a few seconds or hundredths of milliseconds, but which have the disadvantage of having a sensitive surface area of the order of 4 to 10 $mm^2$, which is too small for application to stereotaxic imaging. It is possible to increase the field of view by using an optical device, such as a combination of lenses or a fiber-optic image reducer. However, despite this, the final field of view remains smaller than that obtained with systems using photographic film, which leads to a reduction in the volume of the object accessible to stereotaxic imaging.

SUMMARY OF THE INVENTION

The object of the invention is to overcome these drawbacks by using a digital detector which moves at the same time as the X-ray tube during the stereotaxic imaging, with the aim of optimizing the accessible volume of the breast to be examined.

With this object, the subject of the invention is a mammograph including an X-ray tube on the one hand and a positioning device comprising a breast support plate and an image receiver on the other hand, the tube being carried by an arm which can be moved in rotation about an axis which is perpendicular to it in order to direct the X-ray beam emitted by this tube, characterized in that the image receiver is a digital detector and is placed on a device allowing its lateral movement in a direction opposite to the direction of movement of the tube during orientations of the beam along directions making an angle $\pm\alpha$ with respect to the normal to the plane of the receiver, so that it is completely illuminated by the X-ray beam emitted, the movements of the tube and of the receiver being simultaneous.

A second subject of the invention is a method of using such a mammograph for taking stereotaxic images, including the following steps:

placing a breast to be radiographed between the X-ray tube and the breast support plate;

movement of the X-ray tube in a direction ensuring an orientation of the X-ray beam making an angle $+\alpha$ with respect to the normal to the plane of the receiver and simultaneous movement of the receiver in the opposite direction so that it is completely illuminated by the X-ray beam;

acquisition and storage in memory of the image obtained on the receiver by an electronic device for processing the image;

movement of the X-ray tube in a direction counter to the preceding movement direction, ensuring an orientation of the X-ray beam making an angle $-\alpha$ with respect to the normal to the plane of the receiver, and simultaneous movement of the image receiver in the opposite direction, so that the receiver is completely illuminated by the X-ray beam;

acquisition and storage in memory of the second image thus obtained, by the image processing device;

calculation of the spatial position of a defined region of the breast by the image processing device producing the stereotaxic location on the basis of the two stored images.

BRIEF DESCRIPTION OF THE DRAWINGS

Other characteristics and advantages of the invention will emerge in the light of the description of the embodiment illustrated by the following figures.

The elements carrying the same references in the various figures fulfil the same functions with a view to the same results.

DESCRIPTION OF PREFERRED EMBODIMENTS

Figure 1:
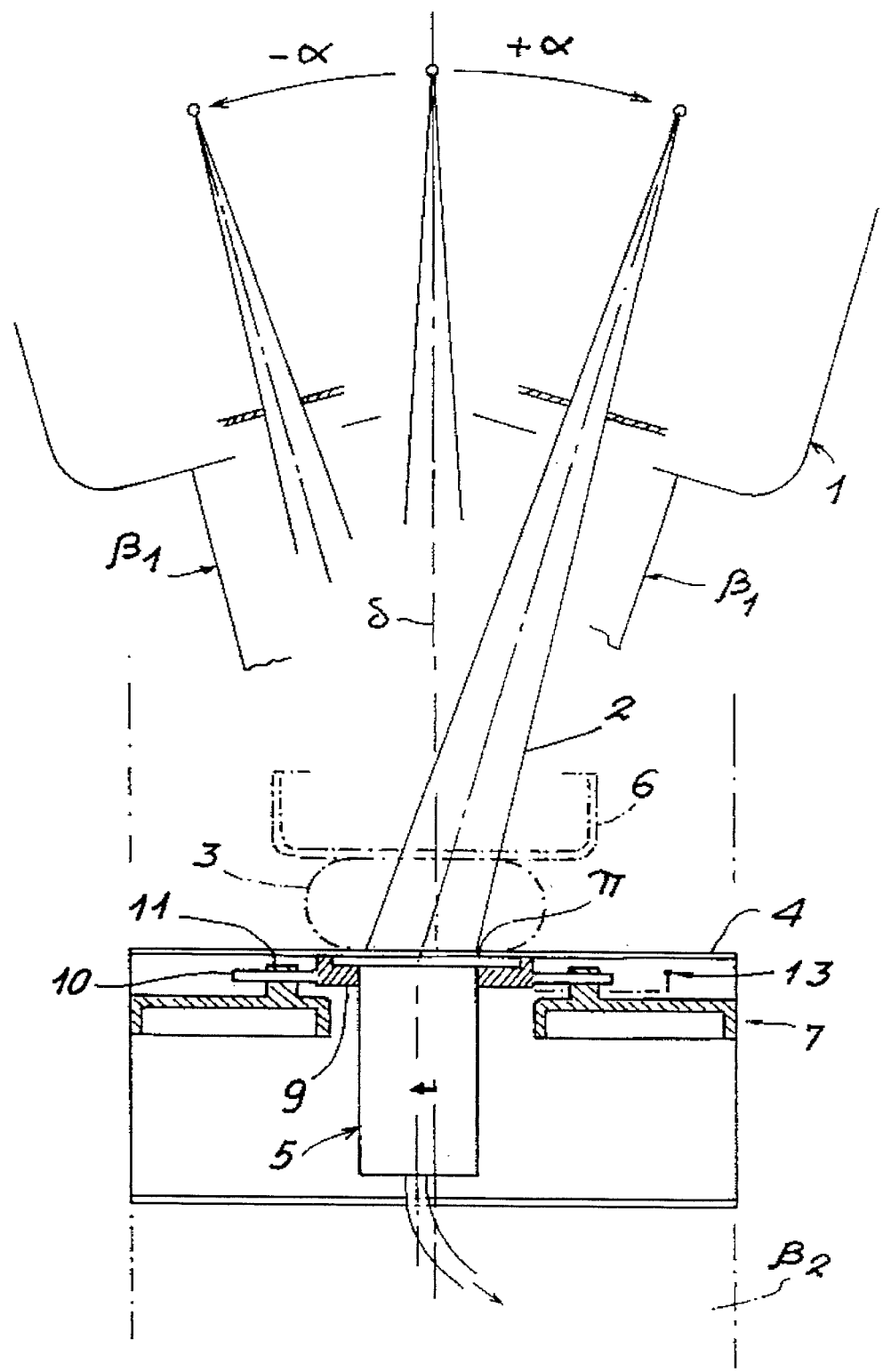
FIG. 1 is a schematic representation of a front view of a mammograph according to the invention, during stereotaxic imaging.

According to FIG. 1, the mammograph according to the invention includes a tube 1 placed at the end of a first arm $\beta_1$ which can be moved about an axis which is perpendicular to it and emitting an X-ray beam 2 toward a breast 3 to be examined, placed on a breast support plate 4, in front of an image receiver 5. A compression plate 6 makes it possible to hold the breast in place during the radiological examination; it is transparent to the X-rays and may be provided with a needle holder device pierced with an orifice for inserting a biopsy needle used in the medical treatments. These two plates 4 and 6 can be adjusted in height with respect to one another and are fixed on another arm $\beta_2$ independent of the first. The arms $\beta_1$ and $\beta_2$ are referred to in FIG. 3. The image receiver 5 is a digital detector placed on a movement device 7. During normal imaging, the X-ray tube 1 is placed above the receiver 5 so as to emit a beam whose axis $\delta$ is perpendicular to the plane $\pi$ of the receiver 5. During stereotaxic imaging, the tube is first inclined so that the axis $\delta$ of the beam 2 emitted has a direction making an angle $+\alpha$ with its preceding direction which was normal to the plane $\pi$ of the receiver 5, then the tube is inclined along an opposite direction so that the axis $\delta$ of the beam 2 makes an angle $-\alpha$ with the normal to the plane $\pi$ of the receiver.

Figure 2:
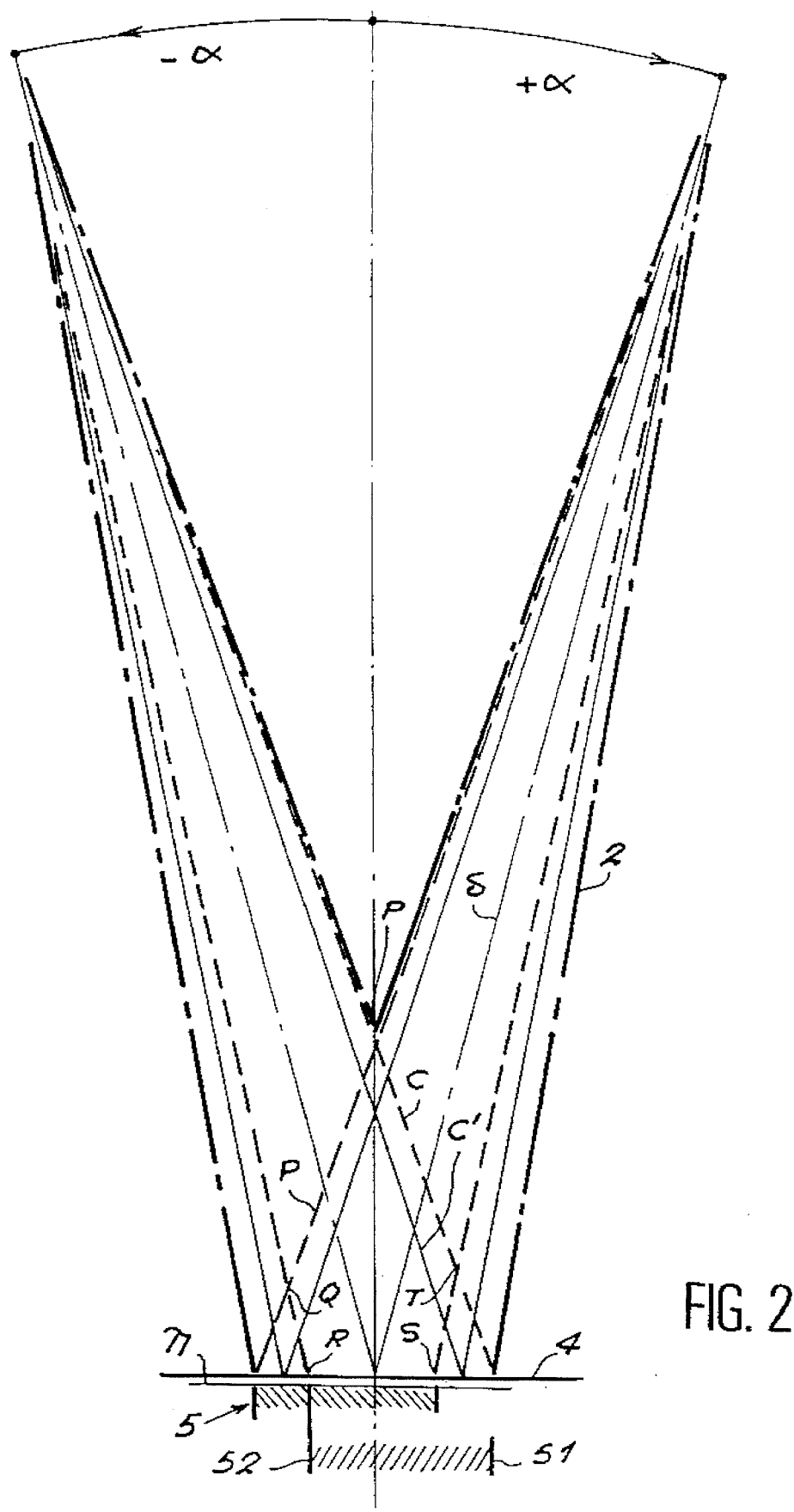
FIG. 2 is a view in a vertical section plane of the X-ray beam emitted during stereotaxic imaging by the mammograph according to the invention.

The X-ray beam emitted during stereotaxic imaging is represented in a vertical section plane in FIG. 2.

In the prior art, in which the receiver is a photographic film whose X-ray sensitive surface area is sufficiently large to receive all of the X-ray beam, symbolically represented in dot and dash lines, the volume accessible by the X-rays is a cone C defined by the intersection of the two beams emitted in the two directions. In the case of a digital detector, such as a CCD camera, the sensitive surface area S of which is smaller than that of a film, and in the absence of movement of this detector with respect to its initial position in its plane $\pi$, it is observed, in the vertical section plane, that the largest surface area accessible by the X-ray beam 2 lies at the base of the cone C' carried by the receiver 5, obtained by overlap of the two parts of the beam leaving the tube 1 and received by the receiver 5, these two parts being symbolically represented by thin continuous lines. Now, this part is unusable because it corresponds to a gap which exists between the breast support plate 4 and the receiver 5. In addition, the clinically most important part often corresponds to the upper point of the triangle: in fact, it is important for the accessible distance at the entry of the breast to be as short as possible, which is why the radiologist will always try to place the breast so as to minimize the path between the lesion and the entry of the breast.

For this purpose, the invention proposes moving the detector 5 in its plane $\pi$ when the X-ray tube 1 has been inclined, during stereotaxic imaging, in a direction opposite to the direction of movement of the tube. The movement of the tube 1 and of the image detector 5 are thus co-ordinated, and may even be simultaneous in certain particular cases. In one particular non-limiting case, the movement is such that, when the camera arrives in abutment at the end of a movement toward the right, or toward the left respectively, the right edge 51, or the left edge 52 respectively, of the image region of the CCD receiver 5 coincides with the position of the right edge, or the left edge respectively, of the image region in the case of the photographic film, defined by the base of the cone C. Thus, the volume accessible by the beam is a polyhedron obtained by the intersection of the two beams bounded by dashes, each ending on the entirety of the detector 5 moved on each shot. In the precise case illustrated by FIG. 2, the accessible volume is generated by a pentagon referenced (PQRST) and the upper part of this pentagon coincides with the upper part of the cone C obtained during stereotaxic imaging on photographic film, the difference between the two accessible volumes appearing at the base.

Figure 3:
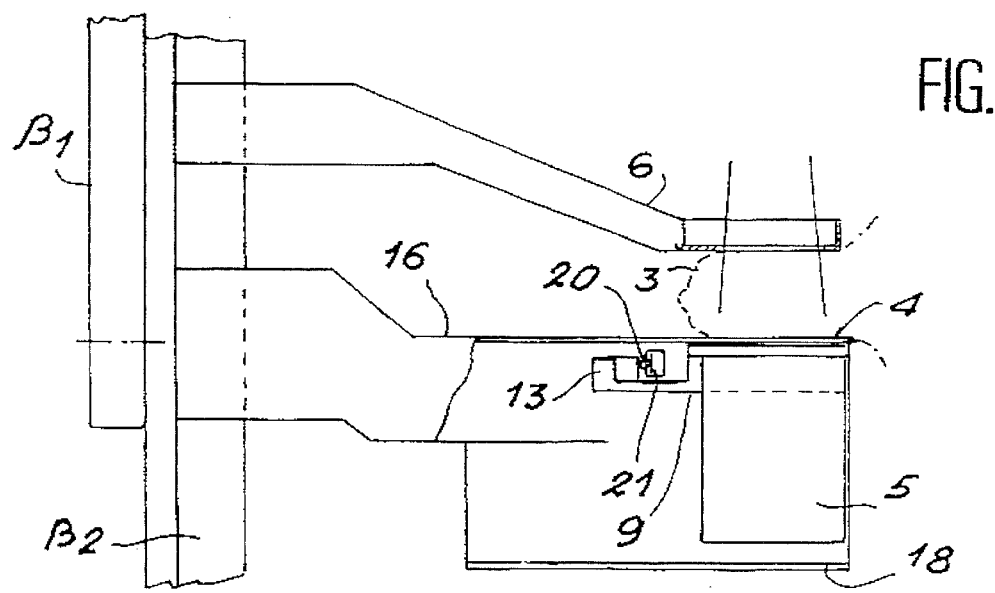
FIGS. 3, 4 and 5 are schematic sectional representations, respectively in a profile view, a plan view and a front view, of the device for moving the image receiver according to the invention.
Figure 4:
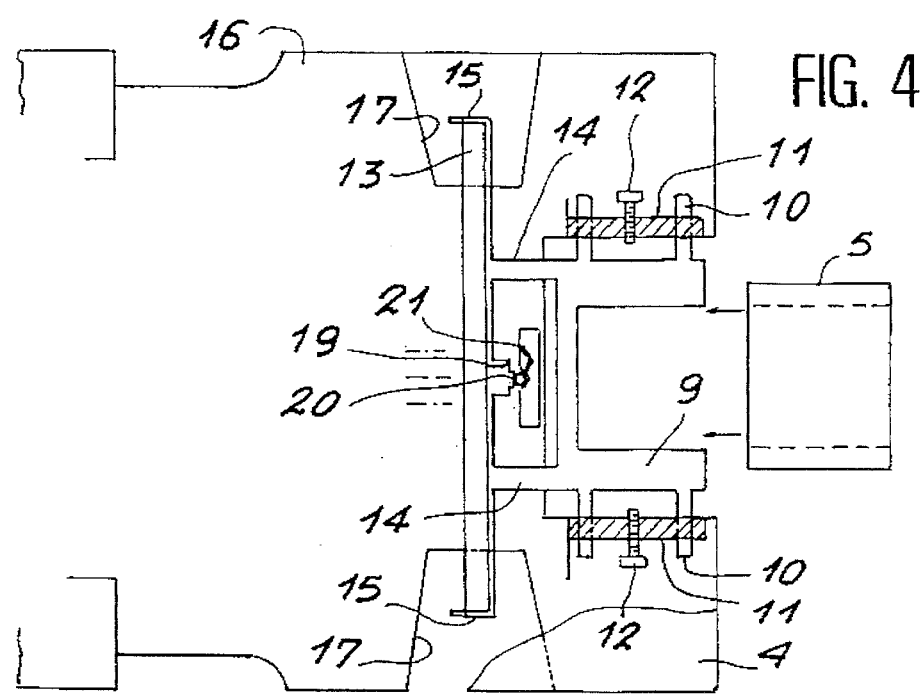
Figure 5:
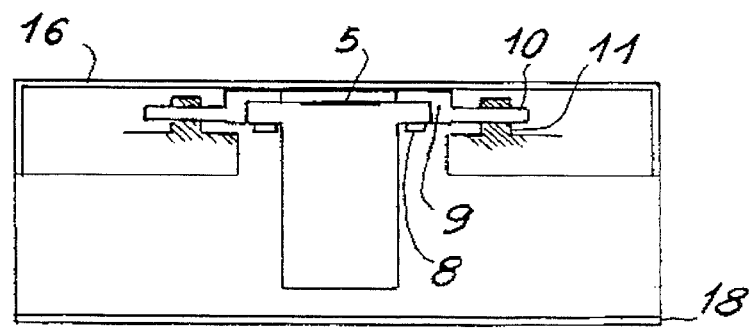

In the example proposed in FIGS. 3, 4 and 5, the digital detector 5 is placed on a movement device 7 comprising a support made from a metal plate 9, and to which the detector 5 is fixed, for example by screws 8. This support rests on two rails 10 parallel to the direction of movement of the detector, at the end of which two stops 11 are arranged, the position of which can be adjusted when installing the mammograph, for example by screws 12. In addition, this support 9 is made integral with an operating member 13, by means of two small bars 14 perpendicular to the movement rails 10, it being possible, for example, for this member to be a bar whose ends 15 are curved so that the operator can grip them easily for moving it. This movement device also comprises a plate 16 for covering the assembly, placed above the sensitive part of the digital detector 5, transparent to the X-rays and having two lateral cutouts 17 above the operating member in order to facilitate the movement thereof, as well as a metal cap 18 situated below the detector and intended to protect the image receiver from external interference. In order for the operator to be able to locate the three possible positions of the receiver with respect to the positions of the X-ray tube, there is a touch location system 19, including a ball 20 accommodated in a central notch 21 for locating the central position, the other two end positions being obtained by bringing the camera to its end-of-travel. It is moved out of the notch under the action of a force.

The movement device might be controlled automatically by a motorization system synchronized with the movements of the X-ray tube.

In practice, the tube is inclined so that the angle between the axis $\delta$ of the X-ray beam and the normal to the plane $\pi$ of the digital detector is approximately 15°.

The performance obtained with the mammograph according to the invention is compared with that obtained with mammographs of the prior art in the following table. Case 1 corresponds to a mammograph whose image receiver includes a photographic film in the shape of a square of side 7.5 cm, while case 2 corresponds to a mammograph whose image receiver is a fixed digital detector in the shape of a square of side 6 cm. Case 3 corresponds to a mammograph according to the invention, the image receiver of which is a digital detector with the same dimensions as the preceding one, but which moves at the same time as the X-ray tube. In all three cases, the distance between the X-ray tube and the image receiver 5 is 480 mm, the distance between the breast support plate 4 and the detector 5 is 10 mm, the angle of rotation of the X-ray tube for taking the stereotaxic images is 15° and the width of the biopsy window is 5.6 cm.

According to the example thus described, it is observed that the invention, represented by case 3, has the following advantages. The distance to the entry of the breast of thickness 6 cm is identical in this case 3 and in case 1 corresponding to a system with a film; on the other hand, this distance is reduced in case 2. As for the working volume of the breast accessible by the mammograph during stereotaxic imaging, it is reduced by less than 10% in the invention compared to what is obtained with a film, while this same volume is reduced by nearly 40% in case 2.

|  | Case 1 | Case 2 | Case 3 |
| --- | --- | --- | --- |
| Size of the detector in cm | 7.5 × 7.5 fixed | 6 × 6 fixed | 6 × 6 with movement |
| Distance to the entry of a breast of thickness 6 cm, in cm | 2.9 | 1.6 | 2.9 |
| Total surface area in | 44.3 | 28.5 | 39.1 |

|                                                        | Case 1 | Case 2 | Case 3 |
| ------------------------------------------------------ | ------ | ------ | ------ |
| the vertical section plane, in cm$^2$                  |        |        |        |
| Working surface area in the vertical section plane, in cm$^2$ | 40.4   | 25.5   | 36.9   |
| Total volume in cm$^3$                                 | 332    | 171    | 235    |
| Accessible working volume in cm$^3$                    | 226    | 143    | 207    |

A further subject of the invention is a method of using a mammograph whose image receiver is a digital detector intended to take stereotaxic images, including the following steps:

placing a breast to be radiographed between the X-ray tube and the breast support plate;

movement of the X-ray tube in a direction making an angle +α with respect to the normal to the plane of the receiver and simultaneous movement of the receiver in the opposite direction so that it is completely illuminated by the X-ray beam;

acquisition and storage in memory of the image obtained on the receiver by a device for processing the image;

movement of the X-ray tube in a direction counter to the preceding movement direction, making an angle −α with respect to the normal to the plane of the receiver, and simultaneous movement of the image receiver in the opposite direction, so that the receiver is completely illuminated by the X-ray beam;

acquisition and storage in memory of the second image thus obtained;

calculation of the spatial position of a defined region of the breast by the device for stereotaxic location on the basis of the two stored images.

By virtue of the precision obtained for locating a lesion of the breast, the mammograph according to the invention makes it possible not only to examine a breast with a view to locating a possible tumor but also to carry out a medical action, such as a preoperational marking, a cytological puncture, or a microbiopsy for histological purposes. This medical action is carried out using a needle positioned on a needle holder with mechanical movement which is made using potentiometers by an operator. This action is made possible by virtue of the calculation, in real time, of the difference between the position of the tip of the needle and the position of the target which constitutes, for example, the tumour, which calculation is carried out by an electronic computer which delivers the information to a display device placed in front of the operator. The needle with which a biopsy needle holder device is provided, which is fixed to the compression plate, is thus guided in order to come as close as possible to the lesion from which it is desired to take a sample. For this purpose, a position reference of the needle holder with respect to the breast is arranged which should be visible on all the images acquired by the detector, and the method of using the mammograph further includes the following steps:

a step of calculation of the position of the biopsy needle;

a step of calculation and display of the difference between the position of said needle and the position of the target to be reached by the needle;

a step of positioning the needle on the breast by moving the needle holder device.

The mammograph according to the invention offers the advantage of using a digital detector giving images of the object to be examined almost in real time, i.e. an image every 0.5 to 10 seconds with a final field of view as large as that offered by the photographic-film mammographs of the prior art.

What is claimed is:

1. A mammograph comprising:

a positioning device defining a rotation axis, said positioning device including:

an arm $β_2$;

breast support plate connected to said arm $β_2$;

a movement device connected to said arm $β_2$; and a digital detector connected to said movement device, said digital detector having a detection surface defining a plane π;

an arm $β_1$ pivotally connected to said positioning device for pivotally rotating said arm arm $β_1$ around said rotation axis, said arm $β_1$ having an end; and an X-ray tube movably attached to said end of said arm $β_1$, said X-ray tube defining a beam axis δ and being pivotable about said rotation axis so as to move in a first direction that is orthogonal with said rotation axis and direct an X-ray beam, emitted by said X-ray tube, along said beam axis δ, wherein pivoting said X-ray tube within an angle ±α causes said movement device to move said digital detector laterally within said plane π along a second direction that is perpendicular to said rotation axis and opposite said first direction so as to accommodate a position of said X-ray tube within said angle ±α and define a volume of a breast stereotaxically accessible by said X-ray beam as a polyhedron having a first surface and a second surface, said first surface and said second surface meeting and being defined by an intersection of said beam axis δ at an angle +α with said beam axis δ at an angle −α, said X-ray beam being entirely incident said digital detector as said movement device moves said digital detector to accommodate pivotal movement of said X-ray tube.

2. The mammograph according to claim 1, wherein said positioning device further comprises a breast compression plate movably connected to said arm $β_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, to a display device.

3. The mammograph according to claim 1, wherein said movement device includes a support to which said digital detector is fixed, said support including two rails that are parallel to said second direction, said two rails being adjacent two adjustable stops, each of said two adjustable stops being arranged at an end of said two rails, and an operating member including two ends, said support being integral with said operating member.

4. The mammograph according to claim 3, wherein said positioning device further comprises a breast compression plate movably connected to said arm $β_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, to a display device.

5. The mammograph according to claim 3, wherein said movement device further comprises a cover plate placed above a light sensitive part of said digital detector, said cover plate being transparent to X-rays and having two lateral cutouts above said two ends of said operating member in order to facilitate said movement thereof by an operator, and a metal cap situated below said digital detector for protecting said digital detector from external interference.

6. The mammograph according to claim 5, wherein said positioning device further comprises a breast compression plate movably connected to said arm $\beta_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, to a display device.

7. The mammograph according to claim 5, wherein said movement device further comprises a touch location system including a ball accommodated in a notch corresponding to a central position of said digital detector during stereotaxic imaging, said ball being removably accommodated in said notch under an action of force.

8. The mammograph according to claim 7, wherein said positioning device further comprises a breast compression plate movably connected to said arm $\beta_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, to a display device.

9. The mammograph according to claim 7, wherein said operating member is a bar that is arranged parallel to said direction, said two ends being curved.

10. The mammograph according to claim 9, wherein said positioning device further comprises a breast compression plate movably connected to said arm $\beta_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, to a display device.

11. A mammograph comprising:

a positioning device defining a rotation axis, said positioning device including:
an arm $\beta_2$;
breast support plate connected to said arm $\beta_2$;
a movement device connected to said arm $\beta_2$; and
an image receiver connected to said movement device, said image receiver having a detection surface defining a plane $\pi$;

an arm $\beta_1$ pivotally connected to said positioning device for pivotally rotating said arm $\beta_1$ around said rotation axis, said arm $\beta_1$ having an end; and an X-ray tube movably attached to said end of said arm $\beta_1$, said X-ray tube defining a beam axis $\delta$ and being pivotable about said rotation axis so as to move in a first direction that is orthogonal with said rotation axis and direct an X-ray beam, emitted by said X-ray tube, along said beam axis $\delta$, wherein pivoting said X-ray tube within an angle $\pm\alpha$ causes said movement device to move said image receiver laterally within said plane $\pi$ along a second direction that is perpendicular to said rotation axis and opposite said first direction so as to accommodate a position of said X-ray tube within said angle $\pm\alpha$ and define a volume of a breast stereotaxically accessible by said X-ray beam as a polyhedron having a first surface and a second surface, said first surface and said second surface meeting and being defined by an intersection of said beam axis $\delta$ at an angle $+\alpha$ with said beam axis $\delta$ at an angle $-\alpha$, said X-ray beam being entirely incident said image receiver as said movement device moves said image receiver to accommodate pivotal movement of said X-ray tube.

12. The mammograph according to claim 11, wherein said positioning device further comprises a breast compression plate movably connected to said arm $\beta_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, to a display device.

13. The mammograph according to claim 11, wherein said movement device includes a support to which said image receiver is fixed, said support including two rails that are parallel to said second direction, said two rails being adjacent two adjustable stops, each of said two adjustable stops being arranged at an end of said two rails, and an operating member including two ends, said support being integral with said operating member.

14. The mammograph according to claim 13, wherein said positioning device further comprises a breast compression plate movably connected to said arm $\beta_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, in a display device.

15. The mammograph according to claim 13, wherein said movement device further comprises a cover plate placed above a light sensitive part of said image receiver, said cover plate being transparent to X-rays and having two lateral cutouts above said two ends of said operating member in order to facilitate said movement thereof by an operator, and a metal cap situated below said image receiver for protecting said image receiver from external interference.

16. The mammograph according to claim 15, wherein said movement device further comprises a touch location system including a ball accommodated in a notch corresponding to a central position of said image receiver during stereotaxic imaging, said ball being removably accommodated in said notch under an action of force.

17. The mammograph according to claim 16, wherein said operating member is a bar that is arranged parallel to said second direction, said two ends being curved.

18. The mammograph according to claim 17, wherein said positioning device further comprises a breast compression plate movably connected to said arm $\beta_2$, said breast compression plate being fitted with a biopsy needle holder plate that is connected to an electronic computer that calculates, in real time, a position of a biopsy needle and delivers a difference, between said position of said biopsy needle and a position of a target to be reached by said biopsy needle, to a display device.

* * * * *